United States Patent [19]

Bernstein et al.

[11] 4,133,110

[45] Jan. 9, 1979

[54] ARTIFICIAL MODULAR DENTURE

[76] Inventors: Richard Bernstein, 17-85 215th St., Bayside, N.Y. 11361; Joseph P. Matriss, 35 Wallington Ave., Wallington, N.J. 07057

[21] Appl. No.: 769,915

[22] Filed: Feb. 18, 1977

[51] Int. Cl.² ............................................. A61C 13/00
[52] U.S. Cl. .......................................................... 32/2
[58] Field of Search ............................................. 32/2

[56] References Cited

U.S. PATENT DOCUMENTS

| | | | |
|---|---|---|---|
| 3,813,777 | 6/1974 | Handel | 32/2 |
| 3,839,769 | 10/1974 | Hazar | 32/2 |

Primary Examiner—Robert Peshock
Attorney, Agent, or Firm—Leonard W. Suroff

[57] ABSTRACT

One form of artificial modular denture, and the method of producing same, includes an assembly of hard prosthetic teeth permanently secured to a U-shaped hard base structure with a terminus of the hard base structure disposed a short distance rearwardly of the incisor areas of the assembly of the prosthetic teeth, with a palatal vault member adapted to substantially conform with the palatal vault area of the patient's mouth being fitted with the artificial denture. The palatal vault member being selected from a set of palatal vault members having differently contoured configurations, and retaining means is provided for individually releasably connecting the palatal vault members to the assembly so as to permit the selection of the most suitably fitting one of the set of palatal vault members for use as part of the artificial denture.

Another form of artificial modular denture, and the method of producing same, includes a palatal vault member being formed only of deflectibly formable material and capable of being easily deflectibly formed upwardly and set into closely conforming relation with any one of a variety of different palatal vault areas of human mouths for preliminary impression forming of said palatal vault member in any one of several different human mouths. The palatal vault member being removably connected to the base, with the removably connected relationship capable of sustaining the forces applied to the palatal vault member by an uncured hardenably hard liner material in fluid form provided on the palatal vault member and the base recess during insertion in the patient's mouth and forming of the hard uncured material into impression conformance with the palatal vault member and the toothless gum area of the patient's mouth to form a hard liner.

6 Claims, 14 Drawing Figures

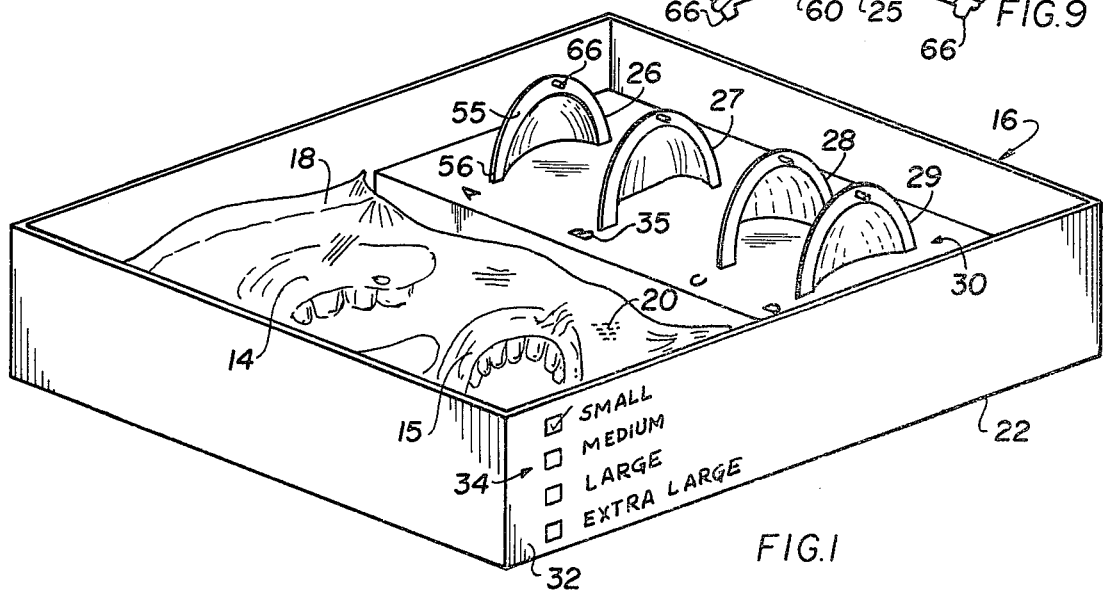

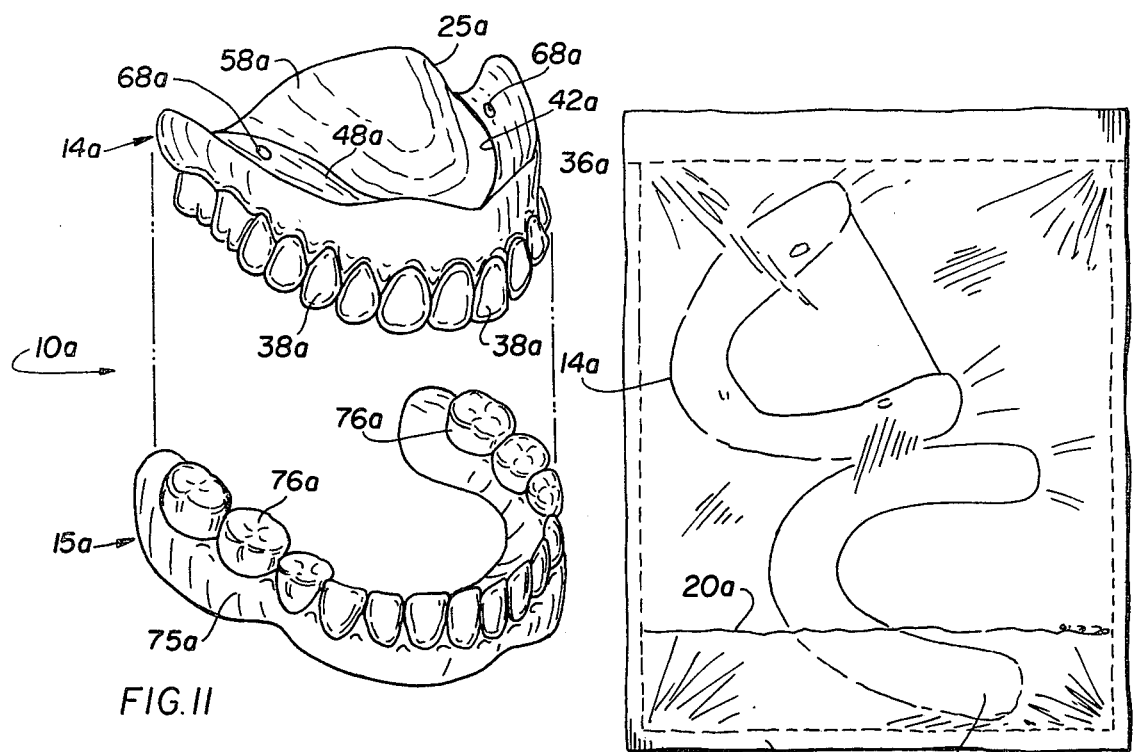
FIG.11
FIG.10
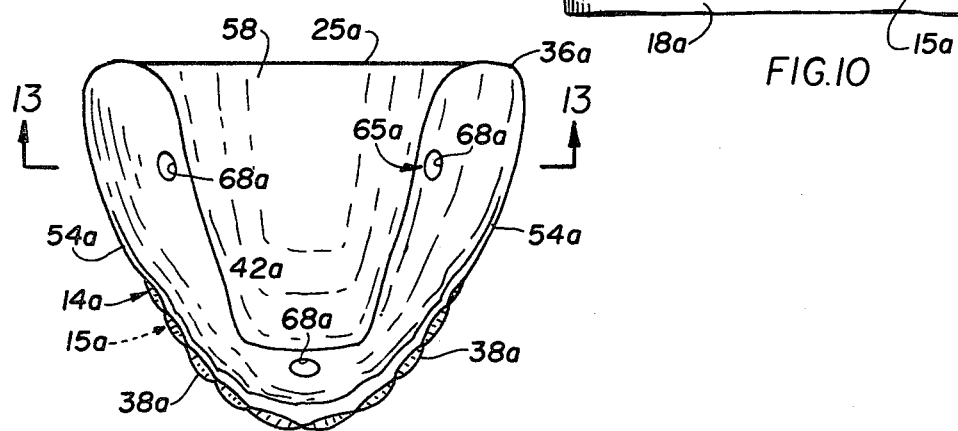
FIG.12
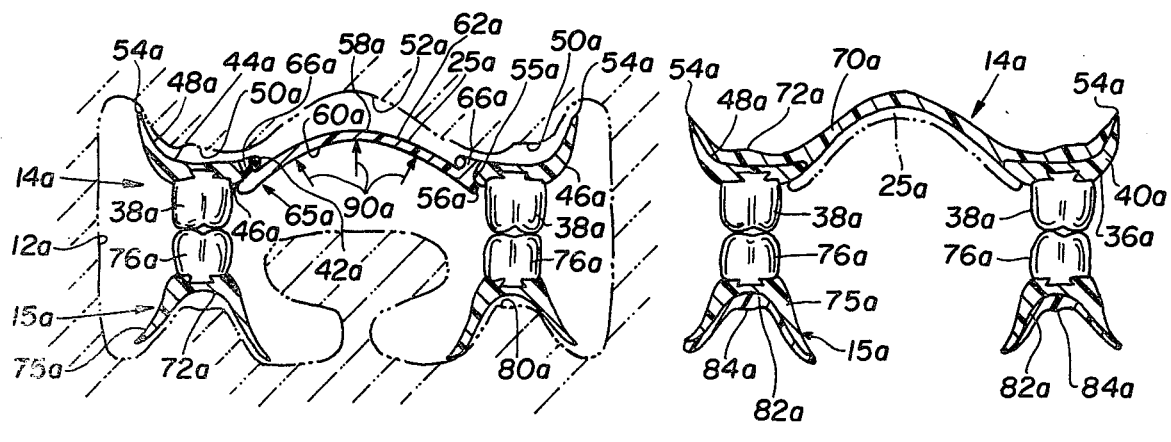
FIG.13
FIG.14

ARTIFICIAL MODULAR DENTURE

BACKGROUND OF THE INVENTION

1. Field Of The Invention

The present invention relates to artificial dentures, and more particularly of the type that the dental profession may adapt to the patient's mouth at a single sitting if desired.

2. Description Of The Prior Art

There are many people who have lost their natural teeth and who, for economic and other reasons, are unable to obtain arificial denture replacements through the services of professional dentistry. Many neglect having proper artificial denture replacements made because of the time consuming element since the fitting work normally requires a great many trips to the dentist's office before a proper and satisfactory fitting of the dentures can be completed.

It has been appreciated in the prior art that the time and costs associated with providing a set of dentures to a patient could be substantially reduced if the artificial or prosthetic denture were previously manufactured and the final fitting to the patient's mouth took place during one or two dental visits. By providing to the dental profession a prosthetic denture that has been previously manufactured on a mass production basis, and that only requires a final fitting to a respective patient, the advantages and cost savings of a mass produced product can be passed along to the patient.

One such form of prosthetic denture manufactured on a mass produced basis is disclosed in U.S. Pat. No. 3,839,796, issued to James M. Hazar, and discloses a denture to be individually fitted to the patient's mouth with a minimum of time involvement by the dentist. The present inventors have found that substantial improvement is obtained over the invention disclosed in the above referenced patent by providing palatal vault members that are either deflectibly formable or provided in a set of different shapes.

In the Hazar patent a palatal member is initially pressure molded having a specific configuration. This configuration is subsequently reheated by the dentist or other licensed denture delivery person, to remold the palatal member to conform to the palatal portion of the patient being fitted with dentures. It has been found that the palatal vault member has a memory to it such that when subsequently subjected to heated liquid above 150° F., there is a softening thereof. Hot coffee can exceed 150° F. Upon this reheating, the palatal vault member desires to return to its original configuration.

The present invention should not be confused with the disclosure in U.S. Pat. No. 2,685,133, issued to B. N. Greene et al, in which the inventors' desire to provide a system wherein the individual who is remote from a dentist, may perform those steps necessary to obtain the impression required to manufacture the dentures. In contrast the present invention permits the obtainment of a finished set of dentures with the patient present.

The present invention is adapted to provide the dentist with a greater degree of flexibility in producing the denture for the patient and the various advantages and distinctions of our invention over the prior art will become more clearly evident as the disclosure proceeds.

OBJECTS OF THE INVENTION

An object of the present invention is to provide an artificial modular preformed full denture which can be fitted by the dentist in a minimum of time, avoiding delays due to frequent fitting appointments with the patient.

Another object of the present invention is to provide a prosthetic denture that includes a set of palatal vault members adapted to be releasably assembled with the denture base structure, so that the dentist may initially select one of the palatal vault members most closely in conformance with the palatal vault area of the patient.

Another object of the present invention is to provide a previously manufactured denture assembly having a plurality of prosthetic teeth permanently secured to the base structure thereof and having means for releasable securement of the individual palatal vault members supplied with the artificial denture, thereby permitting by trial and error the selection of the palatal vault member most closely approximating the palatal vault area of the patient.

Another object of the present invention is to provide an artificial denture which can be assembled precisely, esthetically and rapidly in a minimum of working time.

Another object of the present invention is to provide a previously manufactured denture assembly including a soft deflectibly formable palate vault member that is releasably secured to the base structure of the denture assembly, and which palate vault member is removable from the base structure subsequent to the formation of a self-supporting liner that forms an integral part of the artificial denture.

Another object of the present invention is to provide an artifical denture in which the palatal vault area is formed within the patient's mouth and the structure supporting same during the formation of the palatal vault area is subsequently removed from the denture assembly.

Another object of the present invention is to provide a new and novel method for producing an artificial denture with a minimum of time required by the patient as well as the individual preparing the denture, such as a dentist.

Another object of the present invention is to provide a new and novel method in which the dentist may selectively try the individual palatal vault members supplied with an upper denture, such that the ideal fit is initially obtained prior to forming a hard liner in bonded relation to the palatal vault member and the gum area of the artificial denture.

Other objects and advantages of the present invention will become apparent as the disclosure proceeds.

SUMMARY OF THE INVENTION

The outstanding and unexpected results obtained by the practice of the method and apparatus of this invention are obtained by a series of features, steps and elements assembled and working together in interrelated combination.

In accordance with a first embodiment of the present invention, an artificial modular denture and the system for producing same is disclosed. The system includes an assembly of hard prosthetic teeth permanently secured to a U-shaped hard base structure with a terminus of the hard base structure disposed a short distance rearwardly of the incisor areas of the assembly of the prosthetic teeth. The base contains a generally U-shaped in cross-section recess coextensive with the assembly of teeth and adapted generally to receive a toothless human gum area.

A plurality of palatal vault members having differently contoured configurations are provided. Each one of the palatal vault members being adapted to substantially conform with a palatal vault area of an individual patient's mouth to be fitted with the artificial denture. Retaining means is provided, for individually releasably connecting each one of the palatal vault members to the assembly so as to permit each one of the plurality of the palatal vault members to be individually connected to the assembly and fitted in a patient's mouth until the selection of the most suitable fitting one of the plurality of palatal vault members for use as part of the artificial denture is determined.

Each one of the palatal vault members is preferably transparent so as to permit internal inspection to aid in the selection of the palatal vault member most suitable for use in providing the artificial denture of the particular patient being fitted.

The palatal vault members may each include a peripherally extending rim portion terminating in a marginal edge with a rigid vault portion extending upwardly from the rim portion and integrally formed therewith, with the marginal edge of each rim portion on each one of the palatal vault members being of substantially equal configuration, and the base includes an upper surface, with the rim portion adapted to extend in abutting engagement with the upper surface.

The retaining means may comprise a plurality of spaced apart cavities formed on the base and a plurality of prongs extending from the rim portion, the prongs adapted to extend within the cavities in removably frictional interfitting relationship. A rigid liner is bonded to the palatal vault member and the generally U-shaped recess. The rigid liner conforms intimately to the features of the palatal vault area and the toothless gum area of the patient's mouth.

A kit for producing the artificial denture described above, in the first embodiment, is disclosed and includes an assembly of hard prosthetic teeth permanently secured to a U-shaped hard base structure with a terminus of the hard base structure disposed a short distance rearwardly of the incisor areas of the assembly of the prosthetic teeth, and a plurality of palatal vault members having a variety of differently contoured configurations. The palatal vault members substantially conforming with a palatal vault area of a patient's mouth and adapted to be removably secured to the base, so as to permit each one of the plurality of palatal vault members to be individually connected to the assembly and fitted in a patient's mouth until the selection of the most suitably fitting one of the palatal vault members for use as part of the artificial denture is determined.

The method of producing the artificial denture described in the first embodiment of the invention is obtained by providing an assembly with the hard prosthetic teeth permanently secured to the U-shaped hard base structure having a terminus disposed a short distance rearwardly of the incisor areas of the assembly of the prosthetic teeth and a recess. By supplying a set of palatal vault members having a variety of differently contoured configurations adapted to substantially conform with the palatal vault area of a patient's mouth, the most suitable palatal vault member may be selected. The palatal vault members are adapted to be individually assembled to the assembly whereby the most suitable fitting one of the set of palatal vault members may be determined.

By inserting the base with the palatal vault member assembled thereon into a patient's mouth being fitted for the artificial denture, it is possible to obtain a properly fitting palatal vault member of the set as part of the artificial denture. Once the selection is made, there is a pouring or placing of an uncured hardenably hard liner material, in fluid form, on the base, the selected palatal vault member, and the recess. The liner may be selected from a variety of well known materials used in dentistry, such as methylmathacrylate. Then by reinserting the modular denture into the human mouth and impression forming the hard uncured material into an impression in conformance with the palatal vault and the toothless gum area of the patient's mouth, the conformable surface is formed.

Thereafter by allowing the uncured hardenable liner to harden over the palatal vault member and to bond thereto to form the rigid liner which conforms intimately to the features of the palatal vault area and the toothless gum area of the mouth, the modular denture is produced. In order to obtain the selection of the suitable palatal vault member, there is first a sequencing which includes assembling each of the palatal vault members to the base in order to select the palatal vault member most properly conforming to the palatal vault of the patient. By forming each one of the set of palatal vault members of a transparent material, an internal inspection may be conducted in selecting the palatal vault member suitable for use in providing the artificial denture of the particular patient being fitted.

In accordance with a second embodiment of the present invention, an artificial denture is formed comprising an assembly of hard prosthetic teeth permanently secured to a U-shaped hard base structure with a terminus of the hard base structure disposed a short distance rearwardly of the incisor areas of the assembly of the prosthetic teeth. The base having a generally U-shaped in cross-section recess coextensive with the assembly of teeth and adapted generally to receive a toothless human gum area.

A palatal vault member is connected to the base rearwardly of the terminus and abridging a central area between the portions of the U-shaped base. The palatal vault member is formed only of a deflectibly formable material and capable of being easily deflectibly formed upwardly and set into closely conforming relation with any one of a variety of different palatal vault areas of human mouths for preliminary impression forming of the palatal vault member in any one of several different human mouths.

A hard liner is formed on the palatal vault member and the base recess from an uncured hardenably hard liner material. The palatal vault member is removably connected to the base during the formation of the hard liner. The palatal vault member is in removably connected relationship and capable of sustaining the forces applied to the palatal vault member by the uncured hardenably hard liner material in fluid form provided on the palatal vault member and the base recess during insertion in the patient's mouth and forming of the hard uncured material into impression conformance with the palatal vault member and the toothless gum area of the patient's mouth to form the hard liner.

The method for producing the artificial denture described in the second embodiment is obtained by providing an assembly of hard prosthetic teeth permanently secured to a U-shaped hard base structure with a terminus of the hard base structure disposed a short distance rearwardly of the incisor areas of the assembly of the prosthetic teeth. The base having a generally U-shaped recess coextensive with the assembly of teeth and adapted generally to receive a toothless human gum area.

A soft deflectibly formable palatal vault member is releasably secured to the base for preliminary impression forming of the palatal vault area of the patient's mouth. This is accomplished by inserting the base and deflectibly formable palatal vault member into a patient's mouth and forming the deflectibly formable palatal vault member into close proximity to the palatal vault area of the patient's mouth. Thereafter by removing the assembly with the palatal vault member secured thereto from the patient's mouth, and placing an uncured hardenably hard liner material, in fluid form, on the palatal vault member and the recess, the final shape of the liner may be formed. This is accomplished by reinserting the denture into the human mouth and reinserting the denture into the human mouth and impression forming the hard uncured material into an impression conformance with the palatal vault and the toothless gum area of the patient's mouth. Then allowing the uncured hardenable liner to harden over the recess, and the deflectibly formable palatal vault member in unbonded relation thereto, so as to form a rigid liner which conforms intimately to the features of the palatal vault area and the toothless gum area of the patient's mouth. The dentist or other licensed trained person completes the upper denture by removing the deflectibly formable palatal vault member from the assembly whereby the liner material is self-supporting and forms an integral part of the artificial denture.

BRIEF DESCRIPTION OF THE DRAWINGS

Although the characteristic features of this invention will be particularly pointed out in the claims, the invention itself, and the manner in which it may be made and used, may be better understood by referring to the following description taken in connection with the accompanying drawings forming a part hereof, wherein like reference numerals refer to like parts throughout the several views and in which:

FIG. 1 is a perspective view of an artificial denture provided in kit form for ready use by the dentist;

FIG. 2 is a perspective view of the prosthetic teeth assembly with a selected palatal vault member shown in exploded relation thereto;

FIG. 3 is a top plan view of the artificial denture with the palatal vault member assembled therewith;

FIG. 4 is a sectional view taken along lines 4—4 of FIG. 3 and illustrating a set of artificial dentures in accordance with the present invention being fitted within the oral cavity of a particular patient;

FIG. 5 is a view similar to FIG. 4 illustrating the final set of dentures with the rigid liner formed thereon;

FIGS. 6 through 9 are a sectional view of a respective set of palatal vault members having different contoured configurations and adapted to be removably assembled with the assembly illustrated in FIG. 2;

FIG. 10 illustrates another embodiment of the present invention in which a pair of dentures ae provided in a closed package;

FIG. 11 is a perspective view of a set of upper and lower dentures in exploded relationship to each other;

FIG. 12 is a top plan view of the artificial denture illustrated in FIG. 11 having a readily formable palatal vault member in contrast to the previously described embodiment of the present invention;

FIG. 13 is a sectional view taken along lines 13—13 of FIG. 12 and illustrating a set of artificial dentures in accordance with this embodiment of the present invention being fitted within the oral cavity of a particular patient; and FIG. 14 is a view similar to FIG. 13 illustrating the final set of dentures with the palatal vault member being removed.

DETAILED DESCRIPTION OF THE DRAWINGS

Referring to the drawings, there is illustrated in FIGS. 1 through 9 one embodiment of an artificial denture 10 in accordance with the present invention, as well as the method of producing same for use in the oral cavity 12 of a particular patient. Each set of dentures 10 is comprised of an upper artificial denture 14 and a lower artificial denture 15.

To provide ease and convenience for the dentist or other professional that will be fitting the dentures 14 and 15 to a patient, there may be provided a kit 16 that is adapted with all the necessary components in order to produce a set of artificial dentures 10. The kit 16 may be comprised of a container 18 which contains therein the upper denture 14 and lower denture 15, as well as an antiseptic or sterile fluid 20. The container or package 18 is readily opened for removal of the dentures 14 and 15 therein. A carton 22 is provided for containing the packaged dentures 14 and 15 as well as a set of palatal vault members identified by numeral 25. The set 25 of palatal vault members includes a plurality of rigidly formed elements and identified by numerals 26, 27, 28 and 29.

These individual palatal vault members 26-29 may include one end thereof that is adapted to be situated within supporting means 30, within the carton 22, for retaining the individual palatal vault members 26-29 in spaced relationship to each other.

To facilitate use by the dentist, one panel 32 of the carton 22 may have indicia means 34 contained thereon. The indicia means 34 is designed to indicate to the user the specific size of the dentures 14 and 15 packaged therein. The inventors have determined that at least four sizes are required in order to provide a selection of a conformable set of dentures for use on a patient. The indicia means 34 may further include identifying sizes on the supporting means 30 in the form of an identifying symbol indicated by numeral 35. A cover or closure (not shown) may be provided for shipment of the individual container 22. It is appreciated and understood that each kit 16 may include a plurality of denture sets 10, as well as sets 25 of palatal vault members.

Once the dentist has selected the kit he believes most suitable in order to fit the patient with a set of artificial dentures 10, the method hereinafter described may be performed to provide a complete set of dentures to the patient in a minimal amount of time. Accordingly, the kit 16 may be provided in the sizes of Small, Medium, Large and Extra Large, as indicated by indicia means 34.

The artificial denture 14 includes an assembly 36 of hard prosthetic teeth 38 permanently secured to a U-shaped base structure 40 with a terminus 42 disposed a short distance rearwardly of the incisor areas of the assembly 36. The prosthetic teeth 38 may be secured to the base 40 in a conventional manner, as by injection molding. The base structure 40 may be fabricated from various plastic materials such as methylmathacrylate.

The base 40 includes an upper surface 44 and a lower surface 46 from which the teeth 38 extend. The base 40 further includes a generally U-shaped in cross-section recess 48 that is coextensive with the assembly 36 and adapted to generally receive a toothless human gum area 50, as illustrated in FIG. 4. The inner terminus 42 forms a generally U-shaped opening coinciding with the palatal vault portion 52 of the oral cavity 12 of the particular human patient being fitted with the set of dentures 10. The base 40 includes an upper terminal edge 54 which defines the upper end of the assembly 36.

Once the selection of the properly sized assembly 36 has taken place, then the procedure for completing the upper denture 14 can take place. This is accomplished in accordance with the teachings of the present invention, as illustrated in the embodiment of FIGS. 1–9, by providing a set of palatal vault members 25 comprised of a plurality of individual vault members 26–29. Each palatal vault member 26–29 is adapted to substantially conform with the palatal vault area 52 of a particular patient's mouth. The selection required by the dentist is to determine which palatal vault member of the set 25 is in most closely conforming relationship with the palatal vault area 52 of the oral cavity 12 of the patient being fitted.

Each palatal vault member 26–29 includes a peripherally extending rim portion 55 that is adjacent to the terminal or outer margin 56 of the individual palatal vault member. Interposed between each terminal edge 56 is an upper or inner surface 58 and a lower or outer surface 60. The surfaces 58 and 60 may extend in substantially parallel spaced relationship to each other. The surfaces 58 and 60 define the rigid vault portion 62 of each of the vault members 26–29. Each vault portion 62 extends upwardly from the rim portion 55.

The palatal vault members 26–29 are fabricated from a plastic material which is preferably transparent so as to permit internal inspection, within the oral cavity 12, prior to and during the selection of the palatal vault member most suitable for use in providing the artificial denture 14 for the particular patient being fitted.

In order to permit the ready interchangeability of each of the palatal vault members 26–29 with the assembly 36, there is provided retaining means 65. The retaining means 65 permits the assembly of any one of the palatal vault members from the set 25 with the assembly 36 to permit the selection of the most suitably fitting one of the set of palatal vault members 25. The retaining means 65 may comprise a plurality of protrusions or prongs 66, three being illustrated, adapted to extend within mating cavities or apertures 68 in frictional interfitting relationship therewith. The prongs 66 may be integrally formed with the palatal vault members 26–29 and extend downwardly from the lower surface 60 at the rim portion 55. The mating cavities 68, as illustrated in FIGS. 2, 4 and 5, are provided on the upper surface 44 of base 40 inwardly of the terminus 42. The cavities 68 may extend through the base 40 between the respective upper and lower surfaces 44 and 46. One cavity 68 is provided substantially at each end of the U-shaped base 40 and one cavity substantially centrally thereof.

The above relationship of the prongs 66 and cavities 68 permits the necessary interlocking therebetween to provide the retention during fabrication of the artificial denture 14 and yet permit the sequential selection and assembly of the different palatal vault members.

The completed artificial denture 14 also includes a rigid liner or member 70, as illustrated in FIG. 5, permanently bonded to the palatal vault member 27, and the generally U-shaped recess 44. The rigid liner 70 conforms intimately to the features of the palatal vault area 52 and the toothless gum area 50 of the oral cavity 12. The finished liner 70 has a conformable surface 72 which is adapted to be received within the oral cavity 12.

The lower denture 15 similarly is provided with a U-shaped base structure 75 having a plurality of teeth 76 in a U-shaped configuration extending therefrom. A recess 78 is provided to conform to the toothless gum area 80 associated with the lower portion of the oral cavity 12. The recess 78 is similarly provided with a hard liner 82 that has a conformable surface 84 to match the surface configuration of the toothless gum area 80.

By providing individual palatal vault members 26–29, until one is selected, as illustrated in FIGS. 2–4, the dentist can freely interchange the palatal vault members in set 25 until the most properly fitting one is selected. In the instant description of the invention palatal vault member 27 has been found to be most suitable to be incorporated within the final artifical dentures illustrated in FIG. 4. Each palatal vault member 26–29 is designed to be connected by the retaining means 65 to the base 40 rearwardly of the terminus 42 and abridging the central area between the side portions of the U-shaped base 40. The hard teeth 38 also form a U-shaped configuration.

The method of producing the artificial denture 14, illustrated in FIGS. 1–9, is obtained by providing the assembly 36 with the hard prosthetic teeth 38 permanently secured to the U-shaped hard base structure 40 with the terminus 42 of the hard base structure 40 disposed a short distance rearwardly of the incisor areas of the assembly 36 of the prosthetic teeth 38. By supplying a set 25 of palatal vault members 26–29, as in the kit 16, having a variety of differently contoured configurations adapted to substantially conform with the palatal vault area 52 of a patient's mouth, the most suitable palatal vault member may be selected. The palatal vault members are adapted to be individually assembled to the assembly 36 whereby the most suitable fitting one of the set 25 of palatal vault members 26–29 may be determined. This is accomplished by assembling a selected one of the palatal vault members 26–29 to the base 40.

By inserting the base 40 with the palatal vault member assembled thereon into a patient's mouth 12 being fitted for the artificial denture, it is possible to obtain a properly fitting palatal vault member of the set 25 as part of the artificial denture 14. Palatal vault member 27 is illustrated as being selected. Once the selection is made, there is a pouring or placing of an uncured hardenably hard liner material, in fluid form, on the base 40, the selected palatal vault member 27, and the recess 44. The liner may be selected from a variety of well known materials used in dentistry, such as methylmathacrylate. Then by reinserting the modular denture 14 into the human mouth 12 and impression forming the hard uncured material 70 into an impression in conformance with the palatal vault 52 and the toothless gum area 50 of the patient's mouth 12, the conformable surface 72 is formed.

Thereafter by allowing the uncured hardenable liner 70 to harden over the palatal vault member 27 and to bond thereto to form the rigid liner 70 which conforms intimately to the features of the palatal vault area 52 and the toothless gum area 50 of the mouth, the modular denture 14 is formed. In order to obtain the selection of the palatal vault member 27, there is first a sequencing which includes assembling each of the palatal vault members 26–29 to the base 40 in order to select the palatal vault member most properly conforming to the palatal vault 52 of the patient. By forming each one of the set 25 of palatal vault members 26–29 of a transparent material, an internal inspection may be conducted in selecting the palatal vault member suitable for use in providing the artificial denture 14 of the particular patient being fitted.

Accordingly, the procedure for inserting the base 40 and one of the set 25 of the palatal members assembled thereon into a patient's mouth 12 would first include individually selecting in sequence one of the set 25 of the palatal vault members 26–29 that is believed to most closely approximate the palatal vault configuration of the patient's mouth 12, and removably assembling the selected one of the palatal members 26–29 with the base 40 prior to inserting same into the patient's mouth 12.

By selecting in sequence each one of the palatal vault members 26–29 and assembling same with the base 40 until the desired one of the set 25 of the palatal members 26–29 is determined for use in the artificial denture 14, a final fitting is obtained in a minimal period of time. Then by providing another assembly having hard prosthetic teeth 76 to form the lower artificial denture 15, in matching size and color to the previously provided assembly 36 which forms the upper denture 14, the patient may be fitted with a set of artificial dentures 10. The hard liner 82 is provided in the artificial lower denture 15 in the recess 78 and an impression is taken in the mouth 12 of the intended user of the dentures 10.

Accordingly, as described above with respect to FIGS. 1–9, a first embodiment of the present invention has been disclosed. The inventors have found that for certain applications, and in certain situations it may be desirable that the palatal vault member be fabricated from a material, such as wax, that is easily deflectibly formed to a desired configuration prior to forming the liner in the set of dentures.

In the embodiment previously described with respect to FIGS. 1–9, and the second embodiment hereinafter described with respect to FIGS. 11–14, there is no re-forming of a previously fabricated component part. As previously explained, one of the problems of the prior art dentures is that when a previously fabricated denture is reformed, the memory inherent in the plastic is such that it is subject to subsequent softening and deflection and drinking of certain heated liquids. These problems and disadvantages are overcome by the teachings of the present invention.

Referring now to FIGS. 10–14, there is illustrated a second embodiment of the present invention in the form of an artificial denture 10a comprised of an upper denture 14a and a lower denture 15a that may be supplied in a package 18a having a sterile antiseptic solution 20a therein. The dentures 14a and 15a are adapted to be custom fitted within the oral cavity 12a of a particular patient. The lower denture 15a may be in the same form as described in the previous embodiment of the present invention. The upper denture 14a may also be similar in that the base assembly 36a may be as described with respect to the previous embodiment illustrated in FIGS. 1–9.

In the embodiment illustrated in FIGS. 10–14 a single palatal vault member 25a is provided, rather than a set of rigid palatal vault members. The palatal vault member 25a is connected to the base 40a rearwardly of the terminus 42a and abridging a central area between the portions of the U-shaped base 40a. The palatal vault member 25a is formed only of deflectibly formable material and capable of being easily deflectibly formed upwardly and set into closely conforming relation with any one of a variety of different palatal vault areas 12a of human mouths for preliminary impression forming of the palatal vault member 25a in any one of several different human mouths.

In order to permit the fabrication of the denture 14a, the palatal vault member 25a is removably connected to the base 40a. The removably connected relationship is capable of sustaining the forces applied to the palatal vault member 25a by an uncured hardenably hard liner material 70a in fluid form provided on the palatal vault member 25a and the base recess 44a during insertion in the patient's mouth and forming of the hard uncured material into impression conformance with the palatal vault member 25a and the toothless gum area 50a of the patient's mouth to form the hard liner 70a.

Retaining means 65a for providing the removably connected relationship may be provided in the form of a plurality of cavities 68a in the base 40a, on the upper surface 44a, with the palatal vault member 25a adapted to extend within the cavities 68a in frictional interfitting relationship therewith.

The palatal vault member 25a may be fabricated with prongs 66a integrally formed therewith to provide the interlocking, temporary relationship, with the base 40a. As illustrated in FIG. 13, the dentist or other trained individual will applay an upwardly directed force as indicated by arrows 90a, to the lower surface 60a of the palatal vault member 25a. This force is continued until the upper surface 58a is brought into close proximity with the palatal vault area 52a of the patient's mouth. By deflecting the soft deflectibly formable material of vault member 25a, into close conformity with the palatal vault portion 52a, the liner 70a can then be formed.

The thickness of the hard liner 70a may be nominal due to the fact that the palatal member 25a has been previously deflectibly formed into close conformity with the features of the patient's mouth. The hard liner 70a is also deposited on the recess 48a. An artificial denture 14a, as described with respect to FIGS. 10–14 permits the palatal vault member to be readily disconnected from the base 40a when the liner material hardens into liner 70a.

Palatal vault member 25a is provided with a rim portion 55a that extends in abutting relationship or engagement with the lower surface 46a of the base 40a. The palatal vault member 25a is selected preferably from a material that is conformable at room temperature. The material may be a soft base plate wax well known in the dental field. This avoids any steps of first having to heat the palatal vault member 25a. As illustrated in FIG. 13, the completed liner 70a includes a conformable surface 72a that intimately conforms to the toothless gum area 50a and palatal vault area 52a of the oral cavity 12a. Once the liner 70a has hardened, the palatal vault member 25a is readily removed from its engagement with the base 40a.

It is appreciated that other forms of temporary retaining or securement means is contemplated and within the scope of the present invention. One such form includes pressing together the palatal vault member 25a and the base 40a so as to provide sufficient contact to thereafter withstand the forces applied in the direction of arrows 90a. The cavities 68a need not be utilized, and the retaining means 65a, as defined herein, would include the contacting engagement between the rim portion 55a and the lower surface 46a which has been found sufficient.

Accordingly, this embodiment of the invention, illustrated in FIGS. 10-14, permits a denture 14a to be fabricated which has a relatively thin liner 70a thereon which is rigidly formed when hardening. As illustrated in FIG. 14, the final denture 14a has the vault member 25a removed therefrom, and which is illustrated in phantom for purposes of discussion. This provides a lightweight denture 14a since there is not required a palatal vault member that remains subsequent to the formation of the denture 14a. The upper and lower dentures may be the same configuration for both embodiments of the invention. This provides for the dentist the ability to select a rigid or deformable palatal vault construction as illustrated herein.

The method of producing the artificial dentures 10a of the present invention is produced by the dentist or other licensed denture delivery person, by providing the assembly 36a of hard prosthetic teeth 38a permanently secured to the U-shaped hard base structure 40a with a terminus 42a disposed a short distance rearwardly of the incisor areas of the assembly 36a of the prosthetic teeth 38a. The base has a generally U-shaped recess coextensive with the assembly of teeth 38a and adapted generally to receive a toothless human gum area 50a.

By releasably securing a soft deflectibly formable palatal vault member 25a to the base 40a for preliminary impression forming of the palatal vault area 52a of the patient's mouth 12a, the desired impression may be produced with a minimum of effort. Thereafter, by inserting the base 40a and the deflectibly formable palatal vault member 25a into a patient's mouth, and forming the deflectibly formable palatal vault member 25a into close proximity to the palatal vault area 52a of the patient's mouth 12a, the denture 14a is ready for the liner 70a to be formed thereon. Then by removing the assembly 36a with the now formed palatal vault member 25a secured thereto from the patient's mouth 12a, the desired contour of the palatal vault member 25a is now obtained.

Placing of an uncured hardenably hard liner material, in fluid form, on the palatal vault member 25a on the upper surface 58a, and within the recess 48a, prepares the denture 14a for a final impression. This is obtained by reinserting the denture 14a into the human mouth 12a and impression forming the hard uncured material into an impression conformance with the palatal vault area 52a and the toothless gum area 50a of the patient's mouth 12a.

By allowing the uncured hardenable liner to harden over the recess 48a and the deflectibly formable palatal vault member 25a in unbonded relation thereto, a rigid liner 70a is formed which conforms intimately to the features of the palatal vault area 50a and the toothless gum area 52a of the patient's mouth 12a. When the rigid liner 70a is formed, the removing of the deflectibly formable palatal vault member 25a from the assembly 36a leaves the liner material as a self-supporting rigid structure that forms an integral part of the artificial denture 14a.

To facilitate the procedure of forming the artificial modular denture 14a, the fabricating of the deflectibly formable palatal vault member 25a is preferably from a material that is moldable at room temperature. This permits the dentist to remove the upper denture 14a from its shipping container 18a and, after washing of the solution 20a, proceed to take the desired impression. By preparing the hardenable liner 70a from a transparent material, the patient's oral cavity is visible when the denture 14a is worn.

The choice of materials used is that of selecting the hardenable liner 70a from a material that does not bond to the palatal vault member 25a so as to permit ready separation therebetween when the liner hardens. This permits ease in removal of the vault member 25a after the hard liner 70a is formed. In the fabrication of the denture 14a there may be an interlocking of the palatal vault member 25a with the base 40a so as to support the weight of the liner 70a thereon.

The removably connected interlocking relationship permits the palatal vault member 25a to be readily disconnected from the base 40a when the liner material hardens into the liner 70a. This interlocking relationship may be provided by the retaining means 65a for providing the removably connected relationship. The retaining means may include the plurality of cavities 68a in the base 40a with the palatal vault member 25a adapted to extend within the cavities 68a in frictional interfitting relationship therewith. The base 40a includes a lower surface 46a and the palatal vault member 25a has its upper surface 58a in abutting engagement with the lower surface 46a. The dentures 14a and 15a may be fabricated from various materials that are presently in use by the dental profession, such as acrylic plastic materials.

Although illustrative embodiments of the invention have been described in detail herein with reference to the accompanying drawings, it is to be understood tha the invention is not limited to the precise embodiments and that various changes and modifications may be effected therein without departing from the scope or spirit of the invention.

We claim:
1. A method of producing an artificial denture, comprising the steps of:
   A. providing an assembly of hard prosthetic teeth permanently secured to a U-shaped hard base structure with a terminus of said hard base structure disposed a short distance rearwardly of the incisor areas of said assembly of said prosthetic teeth,
   B. supplying a set of palatal vault members having a variety of differently contoured configurations adapted to substantially conform with the palatal vault area of a patient's mouth, said palatal vault members adapted to be individually assembled to said assembly whereby the most suitable fitting one of said set of palatal vault members may be determined,
   C. assembling a selected one of said palatal vault members to said base,
   D. inserting said base with said palatal vault member assembled thereon into a patient's mouth being fitted for the artificial denture so as to obtain a properly fitting palatal vault member of said set as part of the artificial denture,
   E. placing an uncured hardenably hard liner material, in fluid form, on said base and said selected palatal vault member,

F. reinserting the denture into the human mouth and impression forming the hard uncured material into an impression in conformance with the palatal vault and the toothless gum area of the patient's mouth, and G. allowing the uncured hardenable liner to harden over said palatal vault member and to bond thereto to form a rigid liner which conforms intimately to the features of the palatal vault area and the toothless gum area of the mouth.

2. A method as defined in claim 1, and further including the step of sequencing the assembling of each of said palatal vault members to said base in order to select the palatal vault member most properly conforming to the palatal vault of the patient.

3. A method as defined in claim 1, and further including the step of forming each one of said set of palatal vault members of a transparent material whereby an internal inspection may be conducted in selecting the palatal vault member suitable for use in providing the artificial denture of the particular patient being fitted.

4. A method as defined in claim 1, wherein said step of inserting said base and one of said set of said palatal members assembled thereon into a patient's mouth includes the steps of:

a. individually selecting in sequence one of said set of said palatal vault members that is believed to most closely approximate the palatal vault configuration of the patient's mouth, and b. removably assembling the selected one of said palatal members with said base prior to inserting same into the patient's mouth.

5. A method as defined in claim 4, and further including the steps of selecting in sequence each one of said palatal vault members and assembling same with said base until the desired one of said set of said palatal members is determined for use in the artificial denture.

6. A method as defined in claim 1, and further providing another assembly of hard prosthetic teeth to form the lower artificial denture, in matching size and color to said previously provided assembly which forms the upper denture, whereby the patient may be fitted with a set of artificial dentures.

* * * * *